(12) United States Patent
Wang et al.

(10) Patent No.: US 10,793,512 B2
(45) Date of Patent: Oct. 6, 2020

(54) PREPARATION METHOD FOR HIGH PURITY RACEMIC ADRENALINE

(71) Applicant: AMPHASTAR NANJING PHARMACEUTICALS INC., Nanjing (CN)

(72) Inventors: Yin Wang, Nanjing (CN); Aoxiang Zhang, Nanjing (CN); Yonggang Xu, Nanjing (CN); Song Chen, Nanjing (CN); Haoning Zhang, Nanjing (CN)

(73) Assignee: AMPHASTAR NANJING PHARMACEUTICALS INC., Nanjing (CN)

( * ) Notice: Subject to any disclaimer, the term of this patent is extended or adjusted under 35 U.S.C. 154(b) by 0 days.

(21) Appl. No.: 16/646,506

(22) PCT Filed: Mar. 5, 2019

(86) PCT No.: PCT/CN2019/076945
§ 371 (c)(1),
(2) Date: Mar. 11, 2020

(87) PCT Pub. No.: WO2019/154436
PCT Pub. Date: Aug. 15, 2019

(65) Prior Publication Data
US 2020/0270199 A1 Aug. 27, 2020

(30) Foreign Application Priority Data

Feb. 6, 2018 (CN) .......................... 2018 1 0119825

(51) Int. Cl.
*C07C 215/56* (2006.01)
(52) U.S. Cl.
CPC ................. *C07C 215/56* (2013.01)
(58) Field of Classification Search
None
See application file for complete search history.

(56) References Cited

FOREIGN PATENT DOCUMENTS

| CN | 101781220 A | 7/2010 |
|---|---|---|
| CN | 106478433 A | 3/2017 |
| CN | 108329219 A | 7/2018 |

OTHER PUBLICATIONS

International Search Report and Written Opinion Issued for PCT/CN2019/076945.
English Translation of International Search Report and Written Opinion Issued for PCT/CN2019/076945.

*Primary Examiner* — Ana Z Muresan
(74) *Attorney, Agent, or Firm* — Reising Ethington, P.C.

(57) ABSTRACT

Disclosed is a preparation method for a racemic adrenaline as represented by formula II. The method comprises the following steps: compound 1 is directly racemized in an acidic solution to produce compound 2, the acid solution comprising neither sodium bisulfite nor salicylic acid; and specifically comprises (a), in the acid solution of which the pH is 0.5-1.5, compound 1 is placed under the protection of nitrogen gas and, with the reaction temperature being controlled at 75-95° C., stirred and reacted for 1-3 hours; (b) the reaction solution is controlled at a temperature of 5-20° C., into which an activated carbon is added, under the protection of nitrogen gas, stirred for 20-40 minutes, and filtered, then a filtrate is collected; the filtrate is controlled at a temperature of 5-20° C., the pH thereof is adjusted using ammonia to 8.5-9.5, and is filtered when the pH is stabilized, and a filter cake is washed and dried to produce a high purity racemic adrenaline white powder. The weight yield of the product produced per the preparation method of the present invention is greater than 90%, the chromatographic purity is greater than 96%, and the ee value approaches zero; the invention is inexpensive, simple to operate, favors industrialized production, and has a broad application prospect.

8 Claims, 1 Drawing Sheet

PREPARATION METHOD FOR HIGH PURITY RACEMIC ADRENALINE

CROSS-REFERENCE TO RELATED APPLICATION

This application claims the benefit of CN Application No. 201810119825.3 filed on Feb. 6, 2018, the entire contents of which are incorporated herein.

FIELD

The present invention relates to the field of medicine, in particular to a method for preparing high purity racemic adrenaline.

BACKGROUND

Adrenaline (AD, Epinephrine), as a hormone and a neurotransmitter, is the main hormone of adrenal medulla. Its biosynthesis process mainly comprises that: firstly, norepinephrine is formed in medullary chromium cells, and then further subjected to methylation by the action of phenethylamine-N-methyltransferase (PNMT), thereby forming adrenaline. In pharmacology, adrenaline is used to stimulate the heart when the heart is stopped, or to dilate a trachea during asthma. Adrenaline may contract the blood vessels of the skin, mucous membranes and internal organs (such as the kidney), and may expand the coronary artery and vessels of skeletal muscle. In addition, since adrenaline can directly act on coronary blood vessels to cause vasodilation and to improve blood supply to the heart, it may alleviate symptoms such as weak heartbeat, fall of blood pressure, and difficulty in breathing or the like, by using its effect on exciting the heart, contracting blood vessels and relaxing bronchial smooth muscle and so on.

The pharmaceutical adrenaline is R-adrenaline having the structure of Formula I as following:

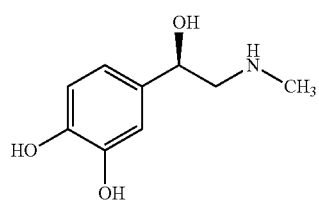

Formula I

R-adrenaline is generally obtained by resolution of racemic adrenaline. However, a mixture of a large amount of S-adrenaline and a small amount of R-adrenaline may be obtained after resolution of the racemic adrenaline under the existing resolution technique. The development of a racemic method for S-adrenaline may greatly reduce the preparation cost of R-adrenaline.

At present, Patent CN101781220B has reported a method for racemization of S-adrenaline by using sodium bisulfite to prepare racemic adrenaline. This method is prone to produce adrenaline sulfonic acid impurities, which have been included in the European Pharmacopoeia.

A recent Patent CN106478433A has reported a process for preparation of racemic adrenaline by using salicylaldehyde and 50% acetic acid. The salicylaldehyde introduced by this process imposes a burden on downstream purification and detection, and the cost of waste liquid recovery and post-treatment generated by 50% acetic acid solution is relatively larger.

Therefore, it is of great commercial value to develop a process that is low-cost, easy to operate, and less waste by optimizations of process conditions and post-treatment methods.

SUMMARY

An object of the present application is to provide a method for preparing high purity racemic adrenaline by using S-adrenaline as a raw material.

In order to achieve the above object, the present application provides the following technique solution: a method for preparing racemic adrenaline of Formula II, comprising the steps of: directly racemizing Compound 1 (S-adrenaline) in an acidic solution to obtain Compound 2, wherein the acidic solution does not include sodium bisulfite or salicylic acid.

As a further improvement, the above preparation method of racemic adrenaline shown as Formula II specifically comprises the following steps: (a) in an acidic solution with a pH of 0.5-1.5, stirring and making Compound 1 react for 1-3 hours at a controlled reaction temperature of 75-95° C. under nitrogen protection; (b) controlling the reaction solution to a temperature of 5-20° C., adding a certain amount of activated carbon into it, and then stirring for 20-40 minutes under nitrogen protection and subsequently filtering with the filtrate being collected; continually controlling the filtrate to a temperature of 5-20° C. and adjusting it to a pH of 8.5-9.5 with ammonia water, and then filtering after the pH is stable; afterwards washing the filter cake and drying to obtain a high purity racemic adrenaline as white powder.

As a further improvement, the acidic solution is an aqueous hydrochloric acid solution, preferably, with a pH of 0.8-1.2. This condition may reduce the degradation impurities caused by the excessive hydrochloric acid, and greatly improve the reaction yield; or may avoid a decreased racemic rate and an increased reaction time due to a too low concentration of hydrochloric acid.

As a further improvement, the nitrogen protection described in the steps (a) and (b) comprises vaccumizing the reaction system to −0.08 MPa or less, and then filling it with nitrogen to atmospheric pressure and sealing it. The amount of impurities is greatly reduced under such conditions.

As a further improvement, the reaction temperature in the step (a) preferably has a range from 80° C. to 85° C., which provide short reaction time and high yield in weight.

As a further improvement, the reaction time in the step (a) is preferably from 1 to 1.5 hours, which provide high chromatographic purity and high yield in weight of the product.

As a further improvement, the amount of the activated carbon in the step (b) is 1-10%, preferably 4-6% of the mass of Compound 1, which provide good decolorization effect and convenient post-treatment.

As a further improvement, the controlled temperature in the step (b) preferably has a range from 5° C. to 10° C., which facilitates the complete precipitation of solid.

As a further improvement, the pH of the solution in step (b) preferably has a range from 9.0 to 9.5, which facilitates the complete precipitation of solid.

Compared with the prior art, some of the advantages of the preparation method disclosed herein are mainly reflected in the following aspects: (1) the production of a large amount of degradation impurities due to overuse of hydrochloric acid may be avoided by controlling the acidic solution to a pH of 0.5-1.5; (2) in the situation where the pH of the solution is selected to be 0.5-1.5, the racemization may be completed within 1-3 hours at a reaction temperature of 75° C. to 95° C. with an ee value close to zero and a high recovery rate; (3) by using the nitrogen protection, the production of a large amount of by-products due to the use of a racemic agent, such as sodium bisulfate or salicylic acid, may be avoided, the reagents may be reduced, and the cost may be lowered; (4) the decolorization of the racemized solution by using 1-10% activated carbon can remove a large amount of impurities without affecting the product yield, while the nitrogen protection is used to avoid the production of oxidized impurities that are difficult to remove. The preparation method disclosed herein may obtain a product which has a chromatographic purity of more than 96%, a yield in weight of more than 90% and an ee value close to zero, also the method is cost effective and easy to operate, and thus is advantageous for industrial production and has a very broad application prospect.

DETAILED DESCRIPTION

In order to help those skilled in the field to understand the contents of the present invention, the technical solutions disclosed herein will be further described below in conjunction with the examples, but the scope of the invention claimed by the appended claims should not be limited by the following contents in any way.

The definitions of "retention time", "peak height", "peak area", "chromatographic purity" and "ee value" and equations in the examples are as follows:

Retention time ($t_R$): the time elapsed from a sample injection to the post-column occurrence of the maximum concentration of a separated component of the sample, that is, the time elapsed from a sample injection to the occurrence of the top point of the chromatographic peak of certain component, is called the retention time of this component, which is expressed as RT and generally using minute (min) as a time unit.

Peak height: a value of the signal which is output from a detector when a component to be tested is eluted from a column to the maximum concentration, that is, the distance from the top point to the bottom of a chromatographic peak, is generally expressed by the unit of the signal output from the detector, and generally use mAU as a unit.

Peak area: a integrated value of peak height and retention time, generally use mAU*s as a unit. In a chromatogram of an analyte to be detected, the total area of the part above a background line indicates the content of the analyte. The larger the area is, the higher the content will be.

Chromatographic purity: the area percentage of the HPLC peak area of a compound to the total HPLC peak area of the sample containing the compound, generally use % as a unit.

ee value: the enantiomeric composition of a compound sample can be described by the term "enantiomeric excess" or "e.e. %", which means an excess of one enantiomer to another enantiomer and generally is expressed in percent (%), and the specific equation is as follows:

$$e.e.\ \% = \frac{S-R}{S+R} \times 100\%$$

Wherein, S: The peak area of S-adrenaline; R: the peak area of R-adrenaline.

Example 1

10 g of S-adrenaline (e.e. % of 36.8%) and 100 ml of purified water were placed into a 250 ml round bottom flask, stirred, and adjusted to a pH of 1.2 with hydrochloric acid. The air in the round bottom flask was replaced with nitrogen. The reaction solution was warmed up to 80±5° C., stirred for 1 h at the temperature, and then was cooled down to 10±5° C. 0.5 g of activated carbon was added, and the air in the round bottom flask was replaced with nitrogen, afterwards the reaction solution was stirred for 30 min and then filtered with the filtrate being collected. The filtrate was kept at 10±5° C. and adjusted to a pH of 9.0 with ammonia water, then was filtrated with the solid being collected. The solid was rinsed with 10 ml of purified water and subsequently with 10 ml of methanol, then was collected and dried to give a solid with a weight of 9.24 g by a yield in weight of 92.4%.

Figure 1:
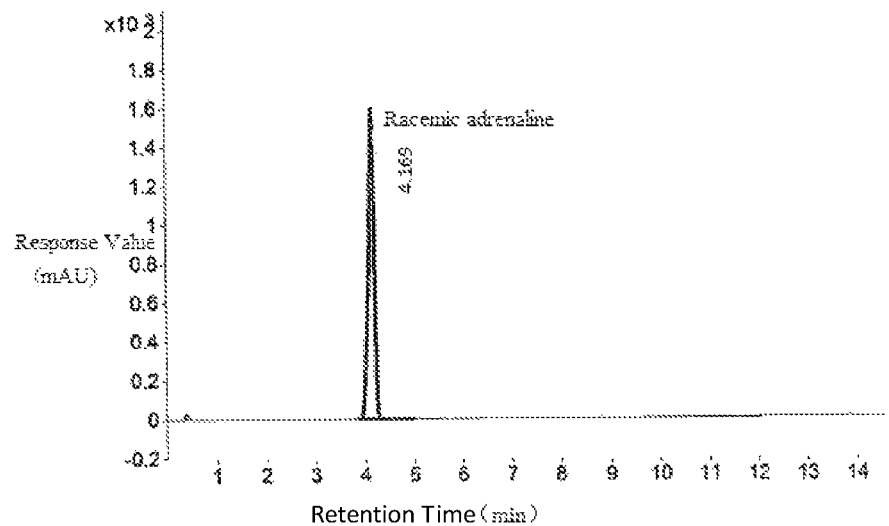
FIG. 1 is a diagram showing an HPLC chromatogram of the purity of racemic adrenaline obtained according to Example 1.

As shown in FIG. 1, the racemic adrenaline has a retention time (RT) of 4.169 min, on a basis of an integrated peak area of 12845.69 mAU*s and a total peak area of 12845.69 mAU*s, a chromatographic purity of 100% is calculated.

Figure 2:
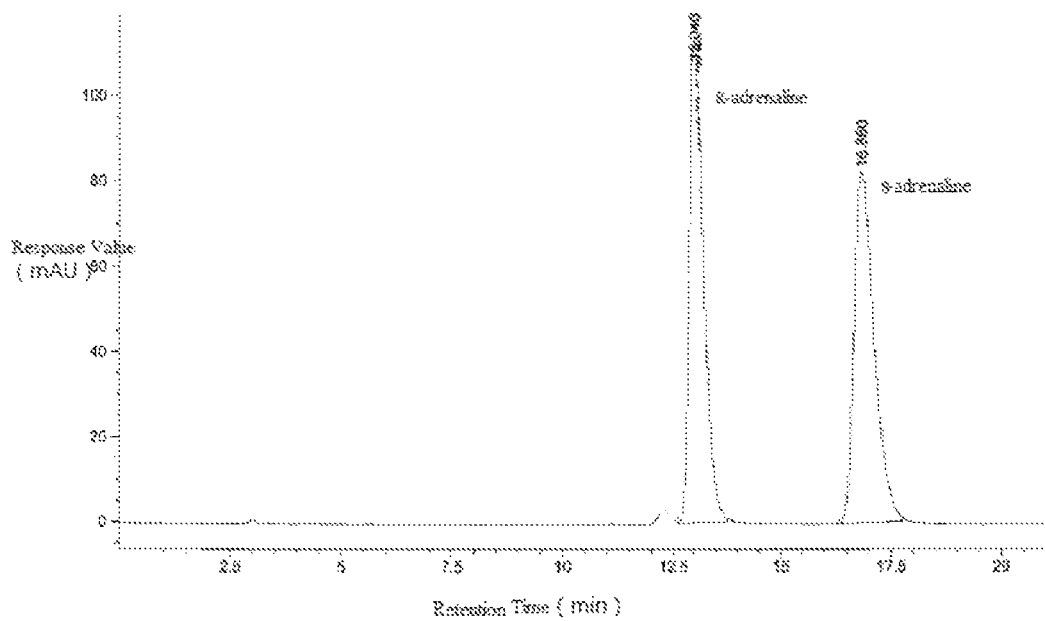
FIG. 2 is a diagram showing an HPLC chromatogram of the ee value detection obtained according to Example 1.

As shown in FIG. 2, the R-adrenaline has a retention time (RT) of 13.046 min and an integrated peak area of 2610.48 mAU*S, and the isomer S-adrenaline has a retention time (RT) of 16.860 min and a peak area of 2611.02 mAU*S;

$$e.e.\ \% = \frac{2611.02 - 2610.48}{2611.02 + 2610.48} \times 100\% = 0.01\%$$

The chromatographic purities and ee values in the following Examples 2 to 5 and Comparative Examples 1 to 2 were all calculated by the same method.

Example 2

10 g of S-adrenaline (e.e. % of 36.8%) and 100 ml of purified water were placed into a 250 ml round bottom flask, stirred, and adjusted to a pH of 1.0 with hydrochloric acid. The air in the round bottom flask was replaced with nitrogen. The reaction solution was warmed up to 80±5° C., stirred for 1 h at the temperature, and then was cooled down to 10±5° C. 0.5 g of activated carbon was added, and the air in the round bottom flask was replaced with nitrogen, afterwards the reaction solution was stirred for 30 min and then filtered with the filtrate being collected. The filtrate was kept at 10±5° C. and adjusted to a pH of 9.0 with ammonia water, then was filtered with the solid being collected. The solid was rinsed with 10 ml of purified water and subsequently with 10 ml of methanol, then was collected and dried to give a solid with a weight of 9.31 g by a yield in weight of 93.1%. The chromatographic purity was 96.3% and the e.e. % was 0.49%.

Example 3

10 g of S-adrenaline (e.e. % of 36.8%) and 100 ml of purified water were placed into a 250 ml round bottom flask, stirred, and adjusted to a pH of 0.8 with hydrochloric acid. The air in the round bottom flask was replaced with nitrogen. The reaction solution was warmed up to 80±5° C., stirred for 1 h at the temperature, and then cooled down to 10±5° C. 0.5 g of activated carbon was added, and the air in the round bottom flask was replaced with nitrogen, afterwards the reaction solution was stirred for 30 min and then filtered with the filtrate being collected. The filtrate was kept at 10±5° C. and adjusted to a pH of 9.0 with ammonia water, then was filtered with the solid being collected. The solid was rinsed with 10 ml of purified water and subsequently with 10 ml of methanol, then was collected and dried to give a solid with a weight of 9.15 g by a yield in weight of 91.5%. The chromatographic purity was 97.8%, and the e.e. % was 0.32%.

Example 4

10 g of S-adrenaline (e.e. % of 36.8%) and 100 ml of purified water were placed into a 250 ml round bottom flask, stirred, and adjusted to a pH of 0.8 with hydrochloric acid. The air in the round bottom flask was replaced with nitrogen. The reaction solution was warmed up to 85±5° C., stirred for 1.5 h at the temperature, and then was cooled down to 15±5° C. 0.6 g of activated carbon was added, and the reaction solution was stirred for 30 min and then filtered with the filtrate being collected. The filtrate was kept at 15±5° C. and adjusted to a pH of 8.5 with ammonia water, then was filtered with the solid being collected. The solid was rinsed with 10 ml of purified water and subsequently with 10 ml of methanol, then was collected and dried to give a solid with a weight of 9.01 g by a yield in weight of 90.1%. The chromatographic purity was 96.8% and the e.e. % was 0.62%.

Example 5

10 g of S-adrenaline (e.e. % of 36.8%) and 100 ml of purified water were placed into a 250 ml round bottom flask, stirred, and adjusted to a pH of 0.8 with hydrochloric acid. The air in the round bottom flask was replaced with nitrogen. The reaction solution was warmed up to 85±5° C., stirred for 3 h at the temperature, and then was cooled down to 15±5° C. 0.4 g of activated carbon was added, and the reaction solution was stirred for 30 min afterwards the reaction solution was filtered with the filtrate being collected. The filtrate was kept at 15±5° C. and adjusted to a pH of 9.5 with ammonia water, then was filtered with the solid being collected. The solid was rinsed with 10 ml of purified water and subsequently with 10 ml of methanol, then was collected and dried to give a solid with a weight of 9.27 g by a yield in weight of 92.7%. The chromatographic purity was 96.1% and the e.e. % was 0.65%.

Comparative Example 1

10 g of S-adrenaline (e.e. % of 36.8%) and 100 ml of purified water were placed into a 250 ml round bottom flask, stirred, and adjusted to a pH of 2.0 with hydrochloric acid. The air in the round bottom flask was replaced with nitrogen. The reaction solution was warmed up to 80±5° C., stirred for 1 h at the temperature, and then was cooled down to 10±5° C. 0.5 g of activated carbon was added, and the air in the round bottom flask was replaced with nitrogen, afterwards the reaction solution was stirred for 30 min and then filtered with the filtrate being collected. The filtrate was kept at 10±5° C. and adjusted to a pH of 9.0 with ammonia water, then was filtered with the solid being collected. The solid was rinsed with 10 ml of purified water and subsequently with 10 ml of methanol, then was collected and dried to give a solid with a weight of 9.36 g by a yield in weight of 93.6%. The chromatographic purity was 92.9% and the e.e. % was 6.97%.

Comparative Example 2

10 g of S-adrenaline (e.e. % of 36.8%) and 100 ml of purified water were placed into a 250 ml round bottom flask, stirred, and adjusted to a pH of 0.2 with hydrochloric acid. The air in the round bottom flask was replaced with nitrogen. The reaction solution was warmed up to 80±5° C., stirred for 1 h at the temperature, and then was cooled down to 10±5° C. 0.5 g of activated carbon was added, and the air in the round bottom flask was replaced with nitrogen, afterwards the reaction solution was stirred for 30 min and then filtered with the filtrate being collected. The filtrate was kept at 10±5° C. and adjusted to a pH of 9.0 with ammonia water, then was filtered with the solid being collected. The solid was rinsed with 10 ml of purified water and subsequently with 10 ml of methanol, then was collected and dried to give a solid with a weight of 8.64 g by a yield in weight of 86.4%. The chromatographic purity was 86.8% and the e.e. % was 0.05%.

What is claimed is:

1. A method for preparing racemic adrenaline of Compound 2, comprising the steps of: directly racemizing Compound 1 in an acidic solution to obtain Compound 2, wherein the acidic solution is an aqueous hydrochloric acid solution, and the acidic solution does not include sodium bisulfite or salicylic acid;

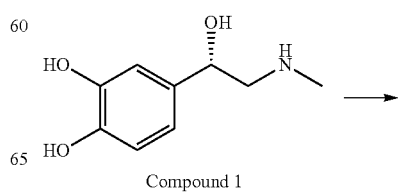

Compound 1

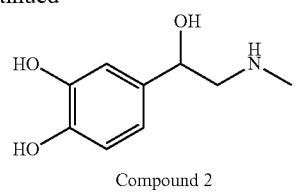

Compound 2 the method further comprising the steps of: (a) in the aqueous hydrochloric acid solution with a pH of 0.5-1.5, stirring and making Compound 1 react for 1-3 hours at a controlled reaction temperature of 75-95° C. under nitrogen protection; (b) controlling the reaction solution to a temperature of 5-20° C., adding a certain amount of activated carbon into it, and then stirring for 20-40 minutes under nitrogen protection and subsequently filtering with the filtrate being collected; continually controlling the filtrate to a temperature of 5-20° C. and adjusting it to a pH of 8.5-9.5 with ammonia water, and then filtering after the pH is stable; afterwards washing the filter cake and drying to obtain a high purity racemic adrenaline.

2. The method for preparing racemic adrenaline according to claim 1, wherein the aqueous hydrochloric acid solution has a pH of 0.8 to 1.2.

3. The method for preparing racemic adrenaline according to claim 1, wherein the nitrogen protection in steps (a) and (b) comprises vacuumizing the reaction system to −0.08 MPa or less, and then filling it with nitrogen to atmospheric pressure and sealing it.

4. The method for preparing racemic adrenaline according to claim 1, wherein the reaction temperature in step (a) has a range from 80° C. to 85° C.

5. The method for preparing racemic adrenaline according to claim 1, wherein the reaction time in step (a) has a range from 1 to 1.5 hours.

6. The method for preparing racemic adrenaline according to claim 1, wherein the amount of the certain amount activated carbon in step (b) is 1-10% the mass of the Compound 1.

7. The method for preparing racemic adrenaline according to claim 1, wherein the controlled temperature in step (b) has a range from 5° C. to 10° C.

8. The method for preparing racemic adrenaline according to claim 1, wherein the pH in step (b) has a range from 9.0 to 9.5.

* * * * *